US007485663B2

(12) United States Patent
Hildesheim et al.

(10) Patent No.: US 7,485,663 B2
(45) Date of Patent: Feb. 3, 2009

(54) CARVEDILOL

(75) Inventors: Jean Hildesheim, Mazkeret Batya (IL); Sergey Finogueev, Quiriat Arbaa (IL); Judith Aronhime, Rechovot (IL); Ben-Zion Dolitzky, Petach Tikva (IL); Shoshana Ben-Valid, Sderot (IL); Ilan Kor, Shoham (IL)

(73) Assignee: Teva Pharmaceutical Industries Ltd., Petach Tiqva (IL)

( * ) Notice: Subject to any disclaimer, the term of this patent is extended or adjusted under 35 U.S.C. 154(b) by 0 days.

(21) Appl. No.: 11/217,643

(22) Filed: Aug. 31, 2005

(65) Prior Publication Data

US 2006/0030614 A1   Feb. 9, 2006

Related U.S. Application Data

(62) Division of application No. 10/758,025, filed on Jan. 16, 2004, now Pat. No. 7,056,942, which is a division of application No. 09/894,798, filed on Jun. 28, 2001, now Pat. No. 6,699,997.

(60) Provisional application No. 60/214,356, filed on Jun. 28, 2000, provisional application No. 60/246,358, filed on Nov. 7, 2000.

(51) Int. Cl.
*A61K 31/403* (2006.01)
*C07C 209/82* (2006.01)

(52) U.S. Cl. ................. 514/411; 548/444; 514/411

(58) Field of Classification Search .......... 548/444; 514/411

See application file for complete search history.

(56) References Cited

U.S. PATENT DOCUMENTS

| 4,503,067 | A | 3/1985 | Wiedemann et al. |
| 4,697,022 | A | 9/1987 | Leinert |
| 4,824,963 | A | 4/1989 | Leinert |
| 4,985,454 | A | 1/1991 | Leinert |
| 5,071,868 | A | 12/1991 | Leinert |
| 5,760,069 | A | 6/1998 | Lukas-Laskey et al. |
| 5,902,821 | A | 5/1999 | Lukas-Laskey et al. |
| 6,022,562 | A | 2/2000 | Autant et al. |
| 6,365,618 | B1 | 4/2002 | Swartz |
| 6,699,997 | B2 | 3/2004 | Hildesheim et al. |
| 6,710,184 | B2 | 3/2004 | Kor et al. |
| 6,730,326 | B2 | 5/2004 | Beyer et al. |
| 6,777,559 | B2 | 8/2004 | Scalone et al. |
| 7,056,942 | B2 | 6/2006 | Hildesheim et al. |
| 7,169,935 | B2 | 1/2007 | Scalone et al. |
| 2002/0099223 | A1 | 7/2002 | Scalone et al. |
| 2004/0127723 | A1 | 7/2004 | Sclaone et al. |
| 2004/0152756 | A1 | 8/2004 | Chen et al. |
| 2004/0171665 | A1 | 9/2004 | Kor et al. |
| 2004/0198812 | A1 | 10/2004 | Bubendorf et al. |
| 2004/0225132 | A1 | 11/2004 | Hildesheim et al. |
| 2005/0240027 | A1 | 10/2005 | Brook et al. |
| 2005/0277689 | A1 | 12/2005 | Brook et al. |
| 2006/0148878 | A1 | 7/2006 | Bubendorf et al. |
| 2006/0167077 | A1 | 7/2006 | Hercek et al. |
| 2006/0270858 | A1 | 11/2006 | Chhabada et al. |
| 2007/0027202 | A1 | 2/2007 | Kumar et al. |
| 2007/0055069 | A1 | 3/2007 | Ramanjaneyulu et al. |
| 2007/0112054 | A1 | 5/2007 | Knipp et al. |
| 2007/0191456 | A1 | 8/2007 | Tarur et al. |
| 2007/0197797 | A1 | 8/2007 | Harrington |

FOREIGN PATENT DOCUMENTS

| CA | 1 259 071 | 9/1989 |
| EP | 0 127 099 A | 12/1984 |
| EP | 0 127 099 B1 | 5/1987 |
| EP | 0 918 055 | 5/1999 |
| WO | WO 99/05105 | 2/1999 |
| WO | WO 01/35938 | 5/2001 |
| WO | WO 01/66702 | 9/2001 |
| WO | WO 02/00216 | 1/2002 |
| WO | WO 03/005970 | 1/2003 |
| WO | WO 03/059807 | 7/2003 |
| WO | WO 2004/041783 | 5/2004 |
| WO | WO 2004/094378 | 11/2004 |
| WO | WO 2005/021504 | 3/2005 |
| WO | WO 2005/080329 | 9/2005 |
| WO | WO 2005/113502 | 12/2005 |
| WO | WO 2005/115981 | 12/2005 |
| WO | WO 2006/061364 | 6/2006 |
| WO | WO 2007/077111 | 7/2007 |
| WO | WO 2007/097504 | 8/2007 |

OTHER PUBLICATIONS

Brittain, H.G. ed. "Polymorphism in Pharmaceutical Sciences," 1999.*
Eagleson, M. "Concise Encyclopedia Chemistry," 1993, pp. 872-873.*
Rouhi, A. M. "The Right Stuff," Chemical & Engineering News, 2003, pp. 31-35.*
"X-Ray Diffraction," U.S. Pharmacopia #23, National Formulary #18 (1995), pp. 1843-1844.*
Chen, et al, "Synthesis and Crystal Structure of Carvedilol," Chinese J. Struct. Chem. (1998), vol. 17(5), pp. 325-328.*
G.M. Wall, "Pharmaceutical Applications of Drug Crystal Studies", Pharmaceutical Manufacturing, vol. 3, No. 2, pp. 33-42, Feb. 1986.
J.K. Haleblian and W. McCrone, "Pharmaceutical Applications of Polymorphism", Journal of Pharmaceutical Sciences, vol. 58, No. 8, pp. 911-929, Jul. 1969.

(Continued)

*Primary Examiner*—Kamal A Saeed
*Assistant Examiner*—Janet L Coppins
(74) *Attorney, Agent, or Firm*—Kenyon & Kenyon LLP

(57) ABSTRACT

This invention relates to an improved process of preparing carvedilol, as well as a new crystalline hydrate and solvate and forms of carvedilol, processes for the manufacture thereof, and pharmaceutical compositions thereof.

5 Claims, 7 Drawing Sheets

OTHER PUBLICATIONS

J.K. Haleblian, "Characterization of Habits and Crystalline Modification of Solids and Their Pharmaceutical Applications", Journal of Pharmaceutical Sciences, vol. 64, No. 8, pp. 1269-1288, Jul. 1975.

Pharmacopeial Forum, vol. 24, No. 1, pp. 5438-5441, Jan.-Feb. 1998.

Senderoff et al., "Synthesis of the Enantiomers and Three Racemic Metabolites of Carvedilol Labeled to High Specific Activity With Tritium", Journal of Labeled Compounds and Radiopharmaceuticals, Dec. 1993, vol. 33, No. 12, pp. 1091-1105.

Chen, Wei-Min et al. "Synthesis and Crystal Structure of Carvediol" Jiegou Huaxue, vol. 17, No. 5, Sep. 1998, pp. 325-328 (abstract included).

Carey, Francis A. et al. "Advanced Organic Chemistry" Third Edition, Part A: Structure and Mechanisms; Plenum Press, pp. 232-239.

Offer of Information, dated Sep. 19, 2007, from corresponding Japanese Patent Application No. 2002-504998.

Japanese Office Action from corresponding Japanese Patent Application No. 2002-504998, mailed May 7, 2008, with English translation.

Experimental Chemistry, 20: Synthesis of Organic Chemistry II, 1956, pp. 497-498, edited by a legally incorporated foundation, Society of Chemistry of Japan, published by Maruzen Co., Ltd.

Experimental Chemistry (Continued), 2: Isolation and Purification, 1967, pp. 184-194, edited by a legally incorporated foundation, Society of Chemistry of Japan, published by Maruzen Co., Ltd.

Experimental Chemistry, $4^{th}$ Edition, 1: Basic Procedures I, 1990, pp. 184-189, edited by a legally incorporated foundation, Society of Chemistry of Japan, published by Maruzen Co., Ltd.

Guidebook of Experimental Chemistry, 1984, pp. 130-131, edited by a legally incorporated foundation, Society of Chemistry of Japan, published by Maruzen Co., Ltd.

Manual of Pharmacology, 1989, $1^{st}$ Edition, pp. 28, 76, 88, edited by Matsumoto Mitsuo, published by Nanzan-do Co., Ltd.

* cited by examiner

CARVEDILOL

CROSS-REFERENCE TO RELATED APPLICATION

This application is a division of prior application U.S. Ser. No. 10/758,025 filed Jan. 16, 2004 now U.S. Pat. No. 7,056,942 which is a division of application Ser. No. 09/894,798 filed Jun. 28, 2001 now U.S. Pat. No. 6,699,997, which claims the benefit of U.S. provisional application Ser. Nos. 60/214,356, filed Jun. 28, 2000 and 60/246,358, filed Nov. 7, 2000, incorporated herein by reference.

FIELD OF THE INVENTION

This invention relates to an improved process of preparing carvedilol, as well as a new crystalline hydrate and solvate and forms of carvedilol, processes for the manufacture thereof, and pharmaceutical compositions thereof.

BACKGROUND OF THE INVENTION

Carvedilol is a nonselective β-adrenergic blocking agent with $\alpha_1$ blocking activity. Carvedilol, also known as (±) 1-(9H-carbazol-4-yloxy)-3-[[2(2-methoxyphenoxy)ethyl]amino]-2-propanol, (CAS Registry No. 72956-09-3) has the structure of formula I.

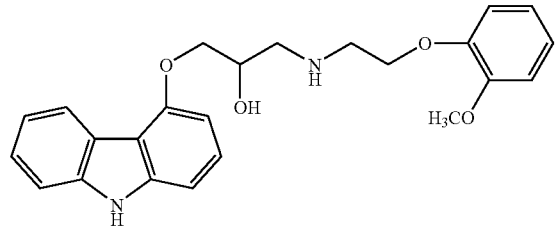

I

Carvedilol has a chiral center and can exist either as individual stereoisomers or in racemic form. Racemic carvedilol is the active ingredient of COREG®, which is indicated for the treatment of congestive heart failure and hypertension. The nonselective β-adrenergic activity of carvedilol is present in the S(−) enantiomer and the $\alpha_1$ blocking activity is present in both the R(+) and S(−) enantiomers at equal potency. Both the racemate and stereoisomers may be obtained according to procedures well known in the art (EP B 0127 099).

Synthesis of Carvedilol

U.S. Pat. No. 4,503,067, which is incorporated herein by reference, discloses a process of preparing carvedilol by the following reaction:

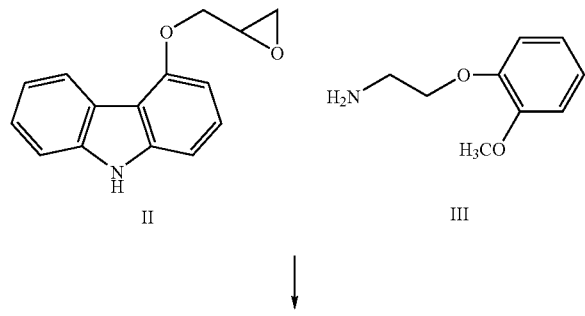

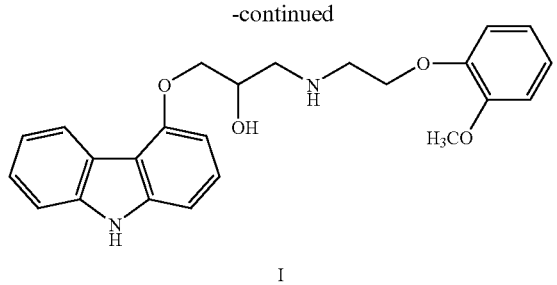

I in which 4-(oxiran-2-ylmethoxy)-9H-carbazole (formula II) is reacted with (2-(2-methoxyphenoxy)ethylamine (formula III) to form carvedilol (I). The above process produces a low yield of carvedilol at least in part because in addition to carvedilol, the process leads to the production of a bis impurity of the following structure (formula IV):

IV

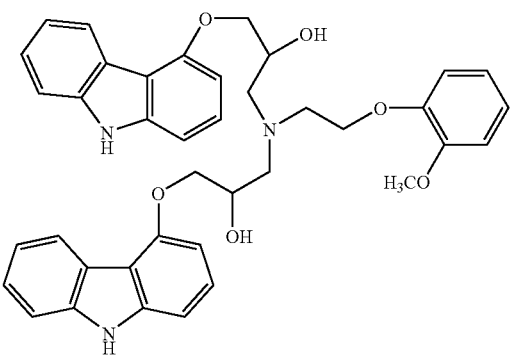

(See EP 918055.)

In order to reduce the formation of the formula IV and to increase the yield of carvedilol, EP 918055 discloses using abenzyl protected form of the 2-(2-methoxyphenoxy)ethylamine (III).

Carvedilol Polymorphs

International application No. WO 99/05105, incorporated herein by reference, discloses that carvedilol can be isolated as two polymorphic forms, depending on the method of preparation. The two polymorphic forms, designated Form I and Form II, are reported to be monotropic and are distinguishable by their infrared, Raman and X-ray powder diffraction spectra. No evidence is found in the literature about the existence of hydrated solvate states of carvedilol.

Polymorphism is the property of some molecules and molecular complexes to assume more than one crystalline form in the solid state. A single molecule may give rise to a variety of crystal forms (also called "polymorphs", "hydrates" or "solvates") having distinct physical properties. For a general review of polymorphs and the pharmaceutical applications of polymorphs see G. M. Wall, *Pharm Manuf.* 3, 33 (1986); J. K. Haleblian and W. McCrone, *J. Pharm. Sci.*, 58, 911 (1969); and J. K. Haleblian, *J. Pharm. Sci.*, 64, 1269 (1975), all of which are incorporated herein by reference.

The existence and physical properties of different crystal forms can be determined by a variety of techniques such as X-ray diffraction spectroscopy, differential scanning calorimetry and infrared spectroscopy. Differences in the physical properties of different crystal forms result from the orientation and intermolecular interactions of adjacent molecules (complexes) in the bulk solid. Accordingly, polymorphs, hydrates and solvates are distinct solids sharing the same molecular formula yet having distinct advantageous and/or disadvantageous physical properties compared to other forms in the polymorph family. The existence and physical properties of polymorphs, hydrates and solvates is unpredictable.

One of the most important physical properties of a pharmaceutical compound which can form polymorphs, hydrates or solvates, is its solubility in aqueous solution, particularly the solubility in gastric juices of a patient. Other important properties relate to the ease of processing the form into pharmaceutical dosages, such as the tendency of a powdered or granulated form to flow and the surface properties that determine whether crystals of the form will adhere to each other when compacted into a tablet.

SUMMARY OF THE INVENTION

The present invention provides a process for preparing carvedilol comprising a step of reacting a compound of formula II, 4-(oxiran-2-ylmethoxy)-9H-carbazole,

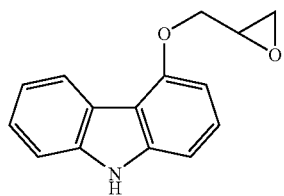

II with a compound of formula III, 2-(2-methoxyphenoxy) ethylamine

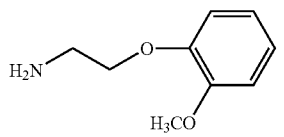

III wherein the compound of formula III is at a molar excess over the compound of formula II.

The present invention further provides crystalline carvedilol hydrate.

The present invention further provides crystalline carvedilol.

The present invention further provides crystalline carvedilol (methyl-ethyl-ketone) solvate.

The present invention further provides crystalline carvedilol Form III characterized by an X-ray powder diffraction pattern having peaks at about 8.4±0.2, 17.4±0.2, and 22.0 ±0.2 degrees two-theta.

The present invention further provides crystalline carvedilol Form IV characterized by an X-ray powder diffraction pattern having peaks at about 11.9±0.2, 14.2±0.2, 18.3±0.2, 19.2±0.2, 21.7±0.2, and 24.2±0.2 degrees two-theta.

The present invention further provides crystalline carvedilol (methyl-ethyl-ketone) solvate Form V characterized by an X-ray powder diffraction pattern having peaks at about 4.1±0.2, 10.3±0.2, and 10.7±0.2 degrees two-theta.

The present invention further provides carvedilol HCl Hydrate characterized by an X-ray powder diffraction pattern having peaks at about 6.5±0.2, 10.2±0.2, 10.4±0.2, 15.8 ±0.2, 16.4±0.2 and 22.2±0.2 degrees two-theta.

The present invention further provides a method for preparing crystalline carvedilol Form I, comprising the steps of dissolving carvedilol in a solution by heating; heating the solution until the crystalline carvedilol is completely dissolved; reducing the temperature of the solution; agitating the solution for a period of time; further reducing the temperature of the solution; further agitating the solution for a period of time; and collecting crystalline carvedilol Form I.

The present invention further provides a method for preparing crystalline carvedilol Form II, comprising the steps of forming a solution of carvedilol by dissolving carvedilol in a solvent; precipitating carvedilol Form II by cooling the solution; and, isolating crystalline carvedilol Form II.

The present invention further provides a method for preparing crystalline carvedilol Form II, comprising the steps of forming a solution of carvedilol by dissolving carvedilol in a solvent mixture; precipitating carvedilol Form II by cooling the solution to about −20° C.; and, isolating crystalline carvedilol Form II.

The present invention further provides a method for preparing crystalline carvedilol Form III, comprising the steps of dissolving carvedilol in a solvent to form a solvent solution; and, precipitating crystalline carvedilol Form III from the solvent solution using water as an anti-solvent.

The present invention further provides a method for preparing crystalline carvedilol Form III, comprising the steps of dissolving carvedilol in a solution by heating; cooling the solution mixture; and, collecting crystalline carvedilol Form III.

The present invention further provides a method for preparing crystalline carvedilol Form IV, comprising the steps of dissolving carvedilol in a solvent to form a solvent solution; adding an anti-solvent to the solvent solution; and, precipitating crystalline carvedilol Form IV from the solvent solution.

The present invention further provides a method for preparing crystalline carvedilol Form V, comprising the steps of dissolving carvedilol in a solvent to form a solvent solution; and, precipitating and isolating crystalline carvedilol Form V from the solvent solution.

The present invention further provides a method for preparing crystalline carvedilol Form V, comprising the steps of dissolving carvedilol in a solvent to form a solvent solution; and, precipitating and isolating crystalline carvedilol Form V from the solvent solution wherein the precipitation step is performed by adding an anti-solvent.

DETAILED DESCRIPTION OF THE INVENTION

Figure 1:
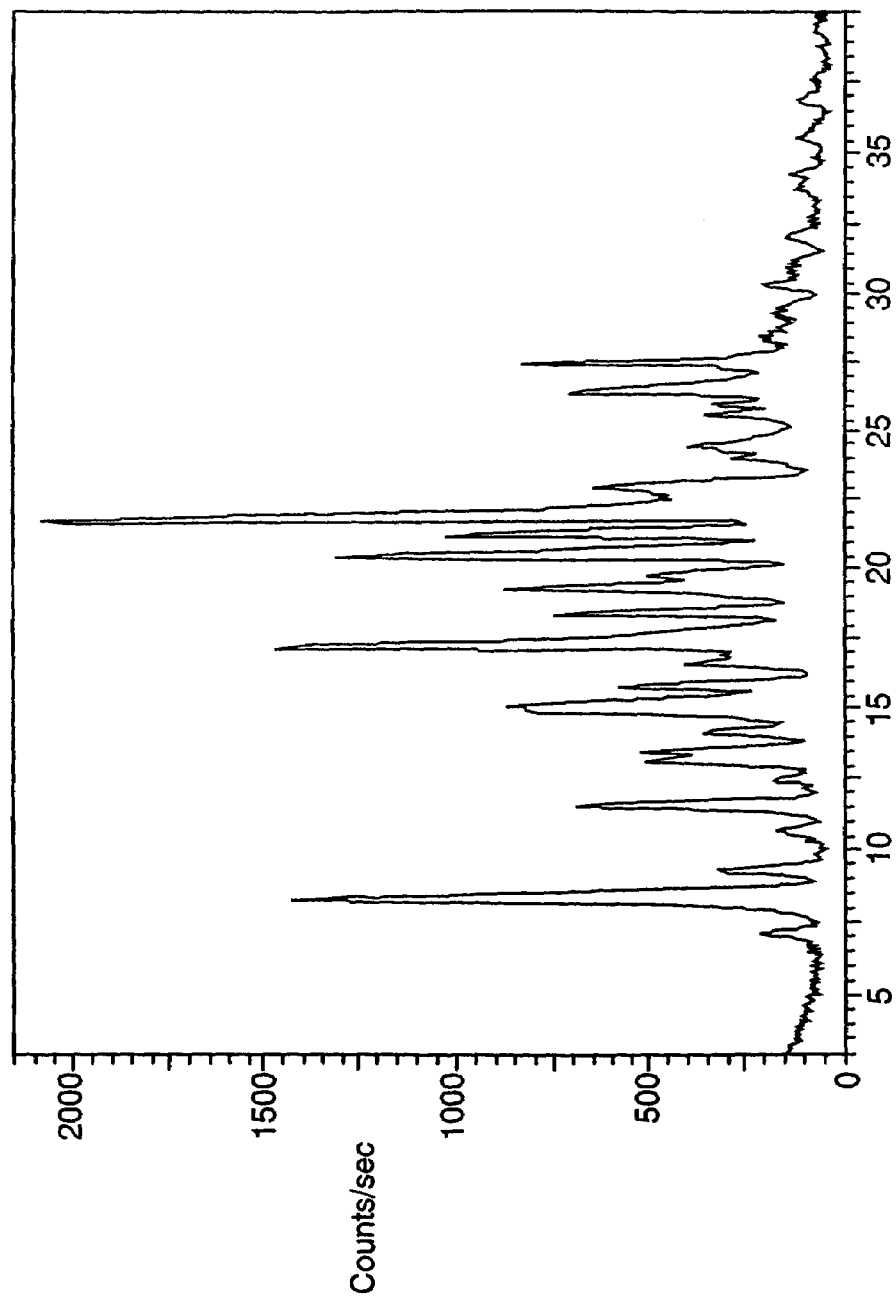
FIG. 1. shows the X-ray diffraction pattern of carvedilol Form III.

As used herein, the term "carvedilol" includes hydrates and solvates of carvedilol. The term "water content" refers to the content of water, based upon the Loss on Drying method (the "LOD" method) as described in Pharmacopeia Forum, Vol.

24, No. 1, p. 5438 (January-February 1998), the Karl Fisher assay for determining water content or thermogravimetric analysis (TGA). The term "equivalents of water" means molar equivalents of water. All percentages herein are by weight unless otherwise indicated. Those skilled in the art will also understand that the term "anhydrous", when used in reference to carvedilol, describes carvedilol which is substantially free of water. One skilled in the art will appreciate that the term "hemihydrate", when used in reference to carvedilol, describes a crystalline material having a water content of about 2.2% w/w. One skilled in the art will appreciate that the term "hydrate", in reference to carvedilol hydrochloride a crystalline material having a water content of about or above 2% w/w. One skilled in the art will also appreciate that the term "solvate of methyl-ethyl-ketone" refers to carvedilol in which solvent is contained within the crystal lattice in quantities above 1%. One skilled in the art will also appreciate that the term "solvate of methyl-ethyl-ketone" which contains one mole of is characterized by a methyl-ethyl-ketone content of about 14% by weight.

Hydrate and solvate forms of carvedilol are novel and distinct from each other in terms of their characteristic powder X-ray diffraction patterns and their thermal profiles.

For the purposes of this specification, ambient temperature is from about 20° C. to about 25° C.

All powder X-ray diffraction patterns were obtained by methods known in the art using a Philips X-ray powder diffractometer. Copper radiation of λ=1.5418 Å was used.

Measurement of thermal analysis are conducted for the purpose of evaluating the physical and chemical changes that may take place in a heated sample. Thermal reactions can be endothermic (e.g., melting, boiling, sublimation, vaporization, desolvation, solid-solid phase transitions, chemical degradation, etc.) or exothermic (e.g., crystallization, oxidative decomposition, etc.) in nature. Such methodology has gained widespread use in the pharmaceutical industry in characterization of polymorphism. Thermal measurements have proven to be useful in the characterization of polymorphic systems. The most commonly applied techniques are thermogravimetry (TGA), differential thermal analysis (DTA), and differential scanning calorimetry (DSC).

The DTA and TGA curves presented herein were obtained by methods known in the art using a DTG Shimadzu model DTG-50 (combined TGA and DTA). The weight of the samples was about 9 to about 13 mg. The samples were scanned up to about 300° C. or above at a rate of 10° C./min. Samples were purged with nitrogen gas at a flow rate of 20 ml/min. Standard alumina crucibles covered lids with one hole.

Thermogravimetry analysis (TGA) is a measure of the thermally induced weight loss of a material as a function of the applied temperature. TGA is restricted to transitions that involve either a gain or a loss of mass, and it is most commonly used to study desolvation processes and compound decomposition.

Karl Fisher analysis, which is well known in the art, is also used to determine the quantity of water in a sample.

As used herein, a solvent is any liquid substance capable of dissolving carvedilol. As used herein, the term "anti-solvent" means a liquid in which a compound is poorly soluble. The addition of an anti-solvent to a solvent reduces the solubility of a compound. As used herein a mixture of solvents refers to a composition comprising more than one solvent.

As used herein, the term "neat" conditions refers to conditions of a reaction wherein the solvent of the reaction is one of the reactants.

Synthesis of Carvedilol

According to one embodiment, the present invention is a process for preparing carvedilol comprising a step of reacting a compound of formula II, 4-(oxiran-2-ylmethoxy)-9H-carbazole,

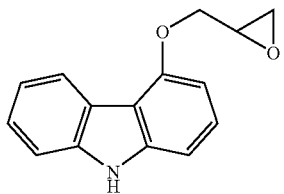

II with a compound of formula III, 2-(2-methoxyphenoxy)ethylamine

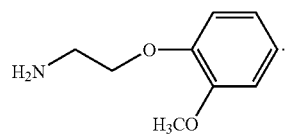

III

The new procedure results in a higher yield of carvedilol than has been reported in the prior art. In addition, the product of the new procedure is nearly free of bis impurities and the reaction is more rapid.

Preferably, the compound of formula III is at a molar excess over the compound of formula II. The compound of formula III and the compound of formula II are preferably at a molar ratio from about 1.5:1 to about 100:1. More preferably, the compound of formula III and the compound of formula II are at a molar ration from about 2.8:1 to about 10:1. Most preferably, the compound of formula III and the compound of formula II are at a molar ratio from about 2.8:1 to about 6:1.

In one embodiment of the present invention, the reacting step is performed in a solvent. The solvent is preferably selected from the group consisting of toluene, xylene and heptane. In an alternative embodiment, the reacting step is performed in a solvent mixture wherein the solvent mixture comprises multiple solvents. Preferably, a solvent of the solvent mixture is selected from the group consisting of toluene, xylene and heptane.

The reacting step is preferably performed at a temperature from about 25° C. and about 150° C. Most preferably, the reacting step is performed at a temperature from about 60° C. and about 120° C.

In an alternative embodiment, the reacting step is performed under neat conditions. The neat conditions may obtained by melting a solid form of the compound of formula III to form a liquid and, dissolving the compound of formula II in the liquid to form a reaction mixture.

The reaction performed under neat conditions may further comprise a step of reducing the temperature of the reaction mixture after dissolving the compound of formula II. The temperature is preferably reduced to about 70° C.

The reaction performed under neat conditions may further comprise a step of adding an organic solvent: water mixture to the reaction mixture. The organic solvent is preferably selected from the group consisting of ethyl acetate, methyl isobutyl ketone, methyl ethyl ketone and butyl acetate.

The reaction performed under neat conditions may further comprise a step of adjusting the pH of the organic solvent: water mixture after it is added to the reaction mixture. The pH is preferably adjusted to less than about pH 5. More preferably, the pH is adjusted from about pH 3 to about pH 5.

Optionally, the process further comprises the steps of isolating carvedilol hydrochloride after adjusting the pH, and purifying carvedilol.

Carvedilol hydrochloride is optionally isolated as a hydrate. Carvedilol HCl isolated as a hydrate typically has an XRD peaks are found at about 6.5±0.2, 10.2±0.2, 10.4±0.2, 14.2±0.2, 14.7±0.2, 16.4±0.2, 17.7±0.2, 20.0±0.2, 21.9±0.2, 25.2±0.2 degrees to 2-theta.

The reaction preformed under neat conditions may further comprise steps of, isolating carvedilol from the reaction mixture after adjusting the pH, and purifying carvedilol. Optionally, carvedilol may be purified by methods well known in the art. (See EP B 0127 099.)

Novel Methods for Preparing Crystalline Carvedilol Form I and Form II

One aspect of the present invention provides a method for preparing crystalline carvedilol Form I, by dissolving carvedilol in a solvent until the crystalline carvedilol is completely dissolved, reducing the temperature of the solution and agitating the solution for a period of time, further reducing the temperature of the solution and agitating the solution for a period of time and, collecting crystalline carvedilol Form I.

The dissolving step is optionally performed by heating the solvent.

The dissolving step is optionally performed by heating crystalline carvedilol at a temperature from about 50° C. 0 to about 60° C. for about 6 hours.

The dissolving step is optionally performed by suspending the crystalline carvedilol in ethyl acetate.

The dissolving step is optionally performed by heating the solution to about 77° C.

The step of reducing the temperature of the solution is optionally performed by cooling the solution to about 50° C. in a time period of 15 min.

The step of agitating solution is optionally performed at about 50° C. for about 48 hours.

The step of further reducing the temperature of the solution is optionally performed by cooling the solution to about 10° C. in about 0.75 hours with agitation.

The step of further agitating the solution is optionally performed by stirring the suspension for more than 5 hours. The step of further agitation may optionally be performed by stirring the suspension for about 24 hours.

The drying step may be performed by heating crystalline carvedilol at a temperature from about 50° C. 0 to about 60° C. for about 6 hours.

The suspending step may be performed by suspending the crystalline carvedilol in ethyl acetate.

The heating step may be performed by heating the solution to about 77° C.

Another aspect of the present invention provides a method for preparing crystalline carvedilol Form II, comprising the steps of forming a solution of carvedilol by dissolving carvedilol in a solvent, precipitating carvedilol Form II by cooling the solution, and isolating crystalline carvedilol Form II.

Optionally, the step of dissolving carvedilol is performed at a temperature from about 40° C. to about the boiling temp of the solvent.

Optionally, the step of cooling the solution is performed by reducing the temperature from about −20° C. to about ambient temperature.

Optionally, the solvent is selected from the group consisting of methanol, absolute ethanol, 1-propanol, isopropanol, n-butanol, ethylene glycol, butyl acetate, isobutyl methyl ketone, dichloromethane, dichloroethane, acetonitrile, acetone, isoamylalcohol, xylene and toluene.

Optionally, the precipitated carvedilol Form II is isolated by filtration.

Another aspect of the present invention provides a method for preparing crystalline carvedilol Form II, comprising the steps of: forming a solution of carvedilol by dissolving carvedilol in a solvent mixture, precipitating carvedilol Form II by cooling the solution to about −20° C., and isolating crystalline carvedilol Form II.

Optionally, the carvedilol is dissolved in a solution at a temperature from about 40° C. to about the boiling temperature of the solvent.

Optionally, the carvedilol Form II is isolated by filtration.

Optionally, the step of cooling the reaction is performed by cooling the solution to a temperature from about −20° C. to ambient temperature.

Optionally, the solvent mixture is selected from the group consisting of acetone: cyclohexane, chloroform: cyclohexane, dichloroethane: cyclohexane, dichloromethane: cyclohexane, pyridine: cyclohexane, tetrahydrofurane:cyclohexane, dioxane: cyclohexane, acetone: hexane, chloroform: hexane, dichloroethane: hexane, dichloromethane: hexane, tetrahydrofuran: hexane and ethanol: hexane.

Novel Carvedilol Polymorphs

In another aspect the present invention provides new crystalline forms of carvedilol, designated Forms III, IV, V and processes for the manufacture thereof. Moreover, the present invention provides a new hydrate form of carvedilol, having water content of about 2% by weight and processes for their manufacture. In another embodiment, the present invention provides new solvate forms of carvedilol, having solvent content up to about 14% by weight, wherein the solvent is methyl ethyl ketone, and processes for their manufacture. These hydrate/solvate forms of carvedilol are useful as intermediates for the synthesis of carvedilol drug substances.

Procedures for Crystallizing Novel Forms of Carvedilol

The novel hydrates/solvates forms provided herein are optionally formed by precipitating carvedilol as a crystalline solid from a solvent or a solvent mixture. It will be understood by those of skill in the art, that other methods may also be used to form the hydrate/solvates form disclosed herein. Alternatively the polymorphs may be formed by routine modification of the procedures disclosed herein.

Formation of Crystalline Carvedilol Form III

One embodiment of the present invention provides a method for preparing crystalline carvedilol Form III, which comprises the steps of forming a solvent solution containing carvedilol; and, precipitating crystalline carvedilol Form III from the solvent solution using water as an anti-solvent. The invention provides for a dissolving step wherein water is present in the solvent solution during the dissolving step. The invention also provides for a precipitation step wherein water is added to the solution after carvedilol is fully dissolved in a solvent.

Optionally, to form the solvent solution containing carvedilol, carvedilol may be dissolved in a solvent at elevated temperature. The preferred elevated temperature is from about 40 to about 90° C. Most preferably the elevated temperature is about 55° C. Alternatively, carvedilol may be dissolved in a solvent at ambient temperature.

Another embodiment of the present invention provides, forming the solvent solution containing carvedilol, by dissolving carvedilol in a solvent and inducing precipitation of crystalline carvedilol Form III by the addition of an anti-solvent. Solvents are optionally selected from the group which includes pyridine, dioxane, isopropanol and chloroform. Anti-solvents are optionally selected from the group which includes water and hexane.

An alternative embodiment of the present invention provides, forming the solvent solution containing carvedilol by dissolving carvedilol in an organic solvent and water and precipitating crystalline carvedilol Form III. In this embodiment the organic solvent is optionally an alcohol. The alcohol is preferably selected from the group consisting of methanol and ethanol. Alternatively, the organic solvent may be selected from the group of solvents consisting of pyridine, dioxane, and ethyl acetate and tetrahydrofurane.

An alternative embodiment of the present invention provides, a method for preparing crystalline carvedilol Form III, comprising the steps of: drying crystalline carvedilol at elevated temperature, suspending crystalline carvedilol in a solution mixture, heating the solution mixture until the crystalline carvedilol is completely dissolved, cooling the solution mixture, and collecting crystalline carvedilol Form III.

Optionally, the drying step may be performed by heating crystalline carvedilol at a temperature from about 50° C. to about 60° C. for about 6 hours.

Optionally, the suspending step may be performed by suspending the crystalline carvedilol in a solution mixture of ethyl acetate: water (150:40).

Optionally, the heating step may be performed by heating the solution mixture from about 60 to about 70° C. with agitation until the crystalline carvedilol is completely dissolved.

Optionally, the cooling step may be performed by cooling the solution mixture to about to 10° C. for a period of about 3 hours with agitation.

Formation of Crystalline Carvedilol Form IV

The present invention also provides a method for preparing crystalline carvedilol Form IV by forming a solvent solution containing carvedilol and inducing precipitation of crystalline carvedilol Form IV by the addition of an "anti-solvent". In this embodiment, solvents are optionally selected from the group which includes methyl ethyl ketone, and methyl isobutyl ketone. Anti-solvents are optionally selected from the group which includes cylcohexane and heptane.

Optionally, to form crystalline carvedilol Form IV carvedilol may be dissolved in a solvent at from below ambient temperature to elevated temperatures. The preferred temperature is from about 10° to about 50° C. Most preferably the temperature is ambient temperature.

Formation of Crystalline Carvedilol Form V

The present invention also provides a method for preparing crystalline carvedilol Form V by forming a solvent solution containing carvedilol and inducing precipitation of crystalline carvedilol solvate Form V by cooling or by adding an anti-solvent. In this embodiment, the solvent is optionally selected from the group which includes methyl ethyl ketone. Anti-solvents are optionally selected from the group which includes cylcohexane and hexane.

Optionally, to form crystalline carvedilol Form V the carvedilol may be dissolved in a solvent solution at elevated temperature. The preferred elevated temperature is from about 10 to about 80° C. Most preferably the elevated temperature is about 55° C. Alternatively, carvedilol may be dissolved in a solvent solution at ambient temperature.

Novel Hydrate and Solvate Crystal Forms of Carvedilol

The present invention provides novel crystal forms of carvedilol which will be designated as Forms III, IV and V, as Well as carvedilol HCl. These forms can be distinguished from the prior art forms of carvedilol and from each other by characteristic powder X-ray diffraction patterns and thermal profiles.

The different crystal forms may also be characterized by their respective solvation state. The most commonly encountered solvates among pharmaceuticals are those of 1:1 stoichiometry. Occasionally mixed solvate species are encountered. When water or solvent is incorporated into the crystal lattice of a compound in stoichiometric proportions, the molecular adduct or adducts formed are referred to as hydrates or solvates.

Crystalline Carvedilol Form III

Carvedilol Form III ("Form III") is characterized by an X-ray diffraction pattern with peaks at about 8.4±0.2, 9.3±0.2, 11.6±0.2, 13.2±0.2, 13.5±0.2, 14.2±0.2, 15.3±0.2, 15.8±0.2, 17.4±0.2, 18.4±0.2, 19.4±0.2, 20.6±0.2, 21.4±0.2, 22.0±0.2, 26.5±0.2 and 27.6±0.2 degrees two-theta. The most characteristic peaks of Form III are at about 8.4±0.2, 17.4±0.2, and 22.0±0.2 degrees two-theta. The diffraction pattern is reproduced in FIG. 1.

Figure 2:
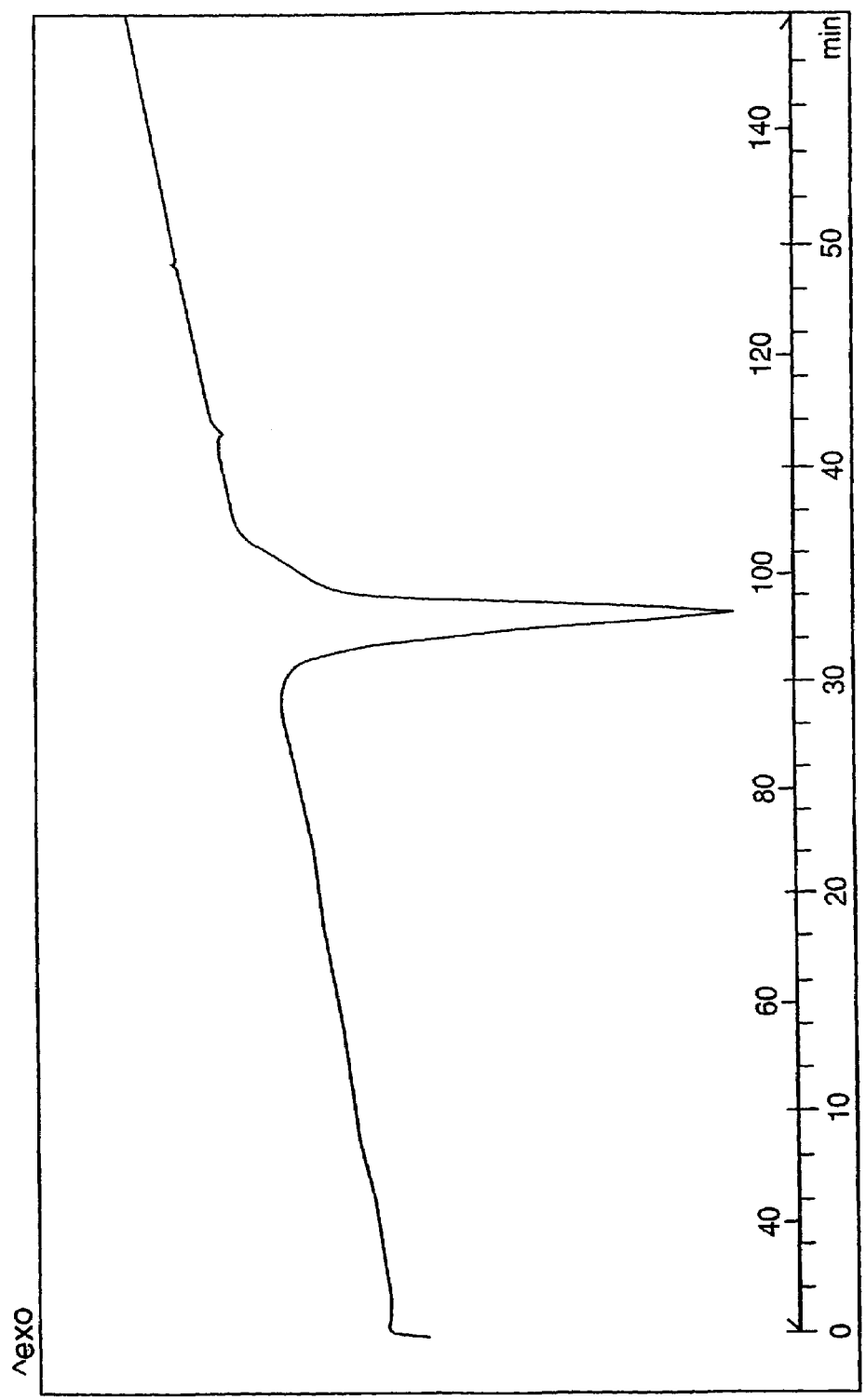
FIG. 2. shows the DTG thermal profile of carvedilol Form III.

The DTG thermal profile of Form IV is shown in FIG. 2. The differential scanning calorimetry (DSC) thermal profile of form III shows one melting peak around 100° C. (96° C.-110° C.), depending on the samples and on the particle size. This melting peak is concomitant to a loss on drying of about 2% as measured by thermal gravimetric analysis (TGA). The amount of water in the sample as determined by Karl Fisher analysis is in good agreement with the value obtained from TGA, thus confirming that the loss on drying is due to the dehydration of water, and indicating that this material is a.

Crystalline Carvedilol Form IV

Figure 3:
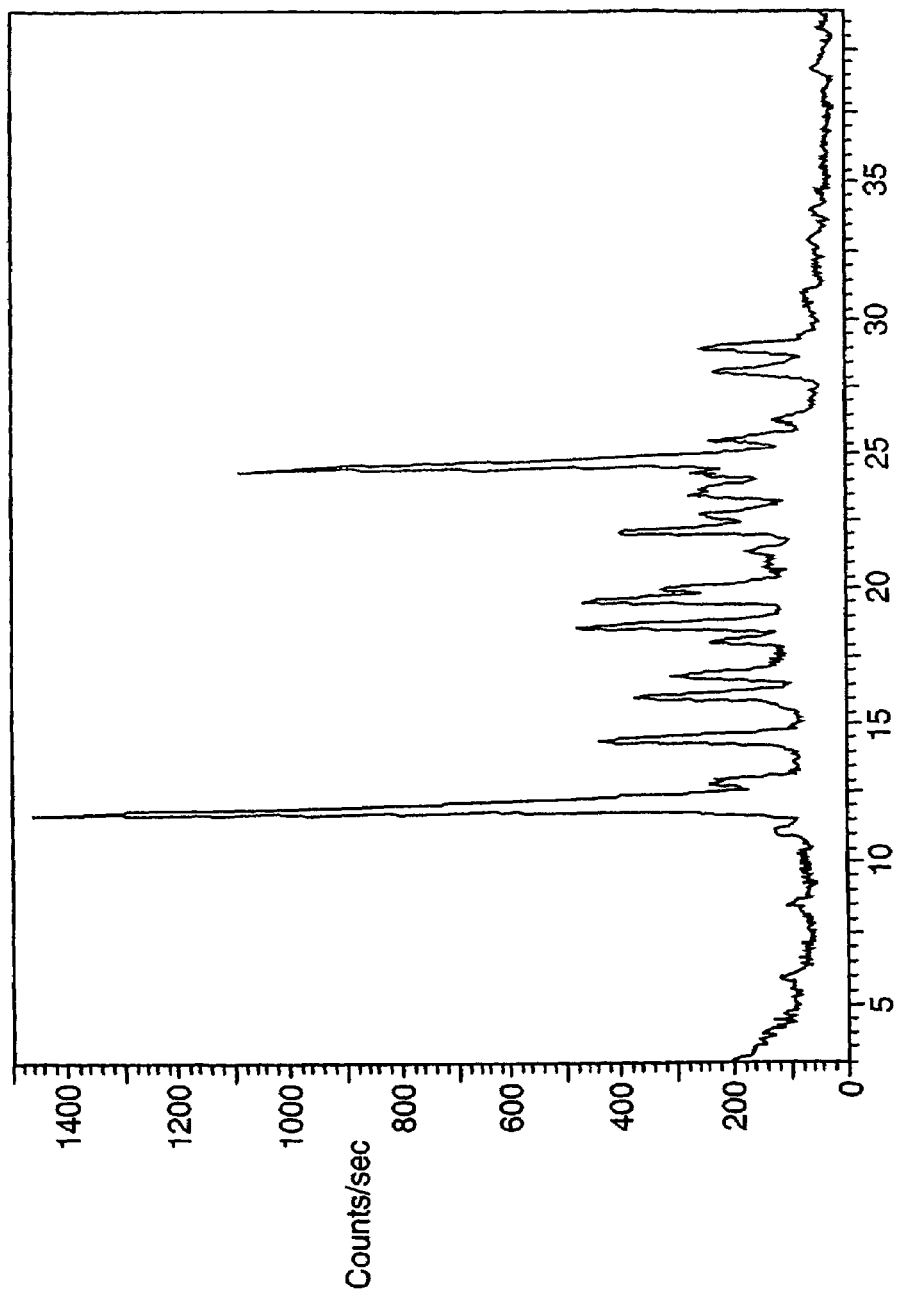
FIG. 3. shows the X-ray diffraction pattern of carvedilol Form IV.

Carvedilol Form IV ("Form IV") is characterized by an X-ray diffraction pattern with peaks at about 11.9±0.2, 14.2±0.2, 15.7±0.2, 16.5±0.2, 17.7±0.2, 18.3±0.2, 19.2±0.2, 19.6±0.2, 21.7±0.2, 22.2±0.2, 23.9±0.2, 24.2±0.2, 24.9±0.2, 27.4±0.2 and 28.2±0.2 degrees two-theta. The most characteristic peaks of Form IV are at about 11.9±0.2, 14.2±0.2, 18.3±0.2, 19.2±0.2, 21.7±0.2, and 24.2±0.2 degrees two-theta. The diffraction pattern is reproduced in FIG. 3.

Figure 4:
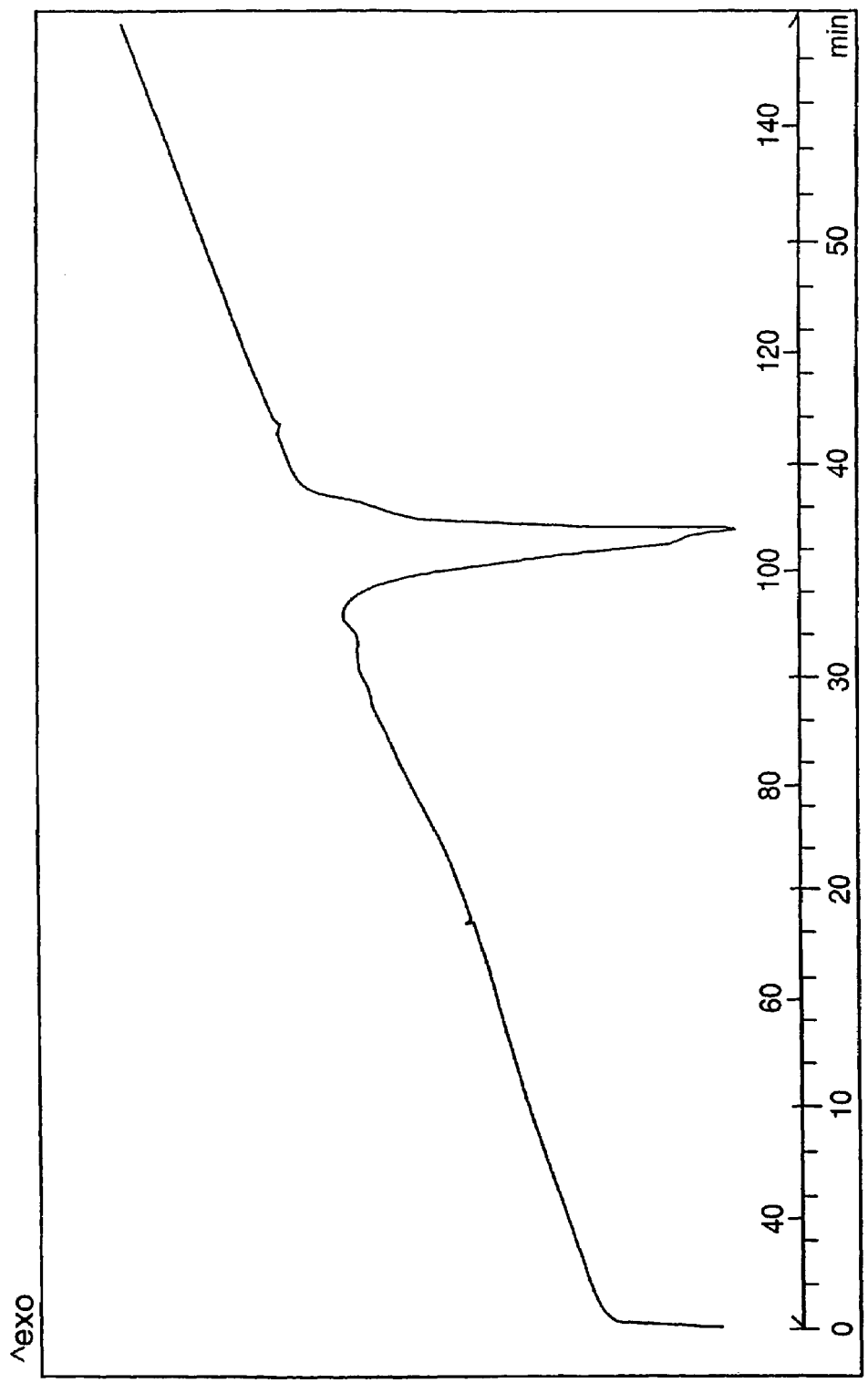
FIG. 4. shows the DTG thermal profile of carvedilol Form IV.

The DTG thermal profile of Form IV is shown in FIG. 4. The DSC thermal profile of form IV shows one melting peak at about 104° C.

Crystalline Carvedilol Form V

Figure 5:
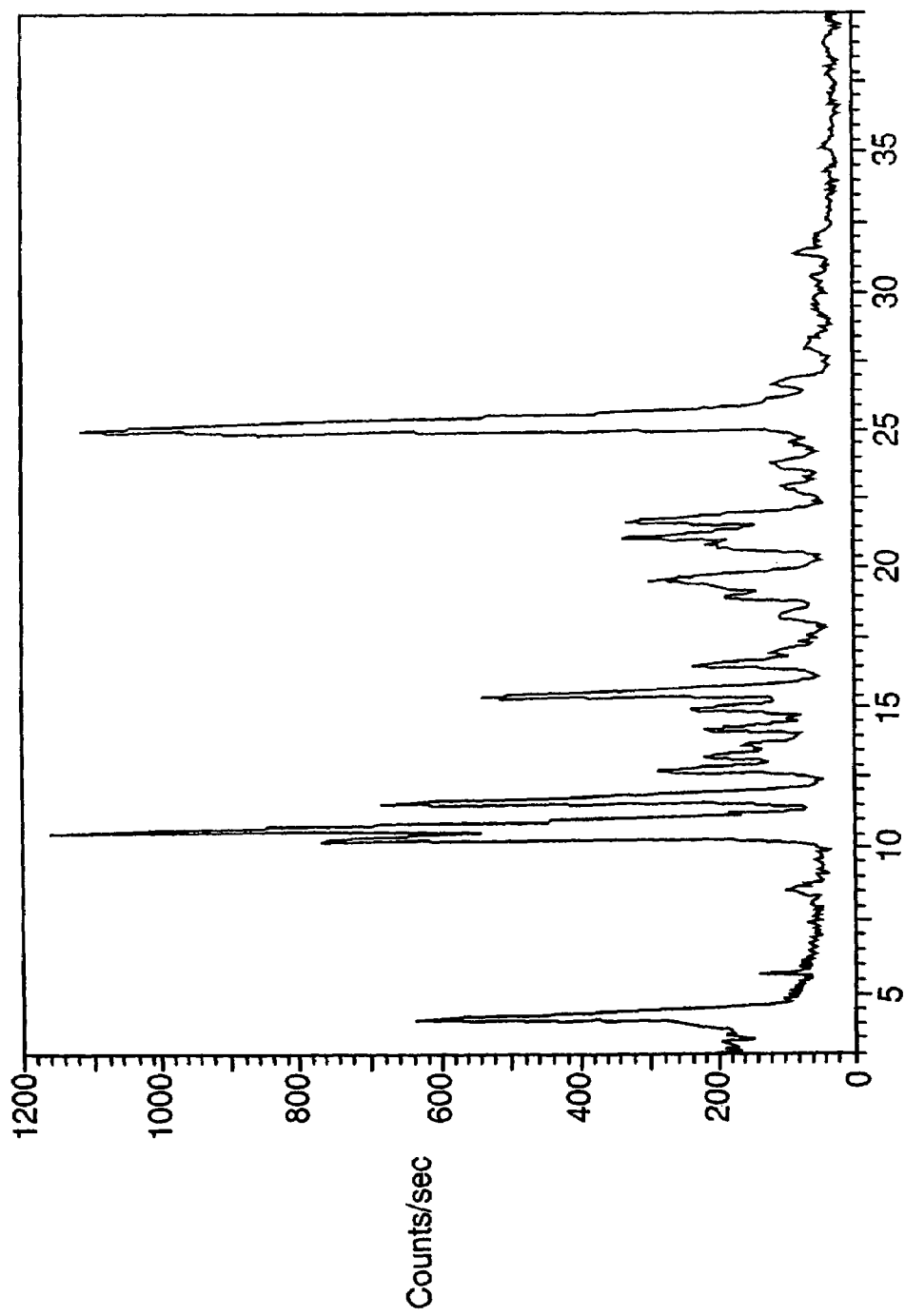
FIG. 5. shows the X-ray diffraction pattern of carvedilol Form V.

Carvedilol Form V ("Form V") is characterized by an X-ray diffraction pattern with peaks at about 4.1±0.2, 10.3±0.2, 10.7±0.2, 11.5±0.2, 12.6±0.2, 14.0±0.2, 14.8±0.2, 15.4±0.2, 16.4±0.2, 16.8±0.2, 18.8±0.2, 20.8±0.2, 21.1±0.2, 21.6±0.2, and 25.4±0.2, degrees two-theta. The most characteristic peaks of Form IV are at about 4.1±0.2, 10.3±0.2, 10.7±0.2 and 11.5±0.2 degrees two-theta. The diffraction pattern is reproduced in FIG. 5.

Figure 6:
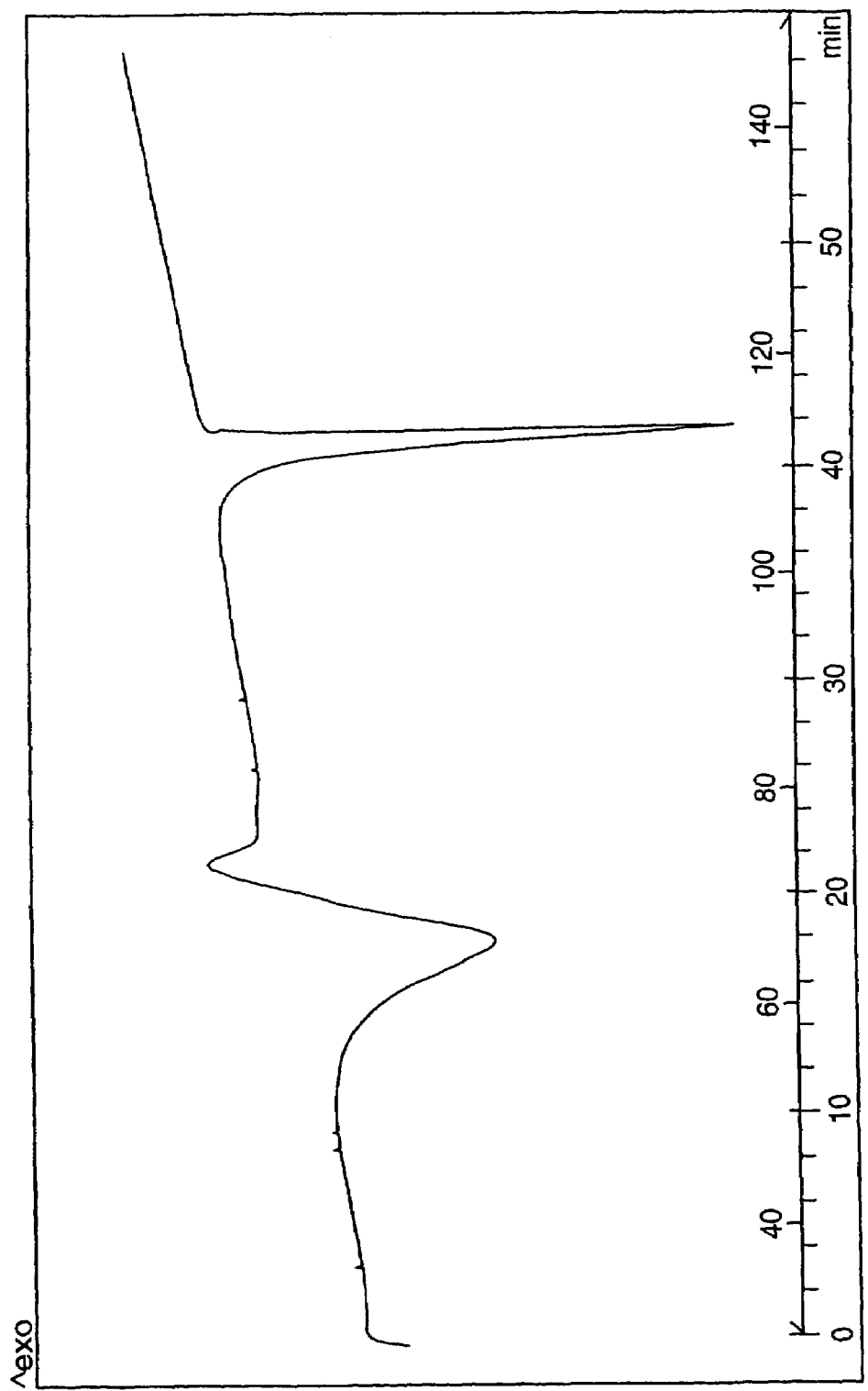
FIG. 6. shows the DTG thermal profile of carvedilol Form V.

The DTG thermal profile of Form V is shown in FIG. 6. The DSC thermal profile of Form V shows a solvent desorption endotherm. at about 67° C., followed by a recrystallization event, and a melting peak at 115° C. The desorption endotherm is concomitant to a loss on drying of about 14% as determined by TGA. This behavior is consistent with the loss of a molecule of MEK per molecule of carvedilol (the calculated stoichiometric value of mono-MEK is 15%).

Carvedilol HCl Hydrate

Figure 7:
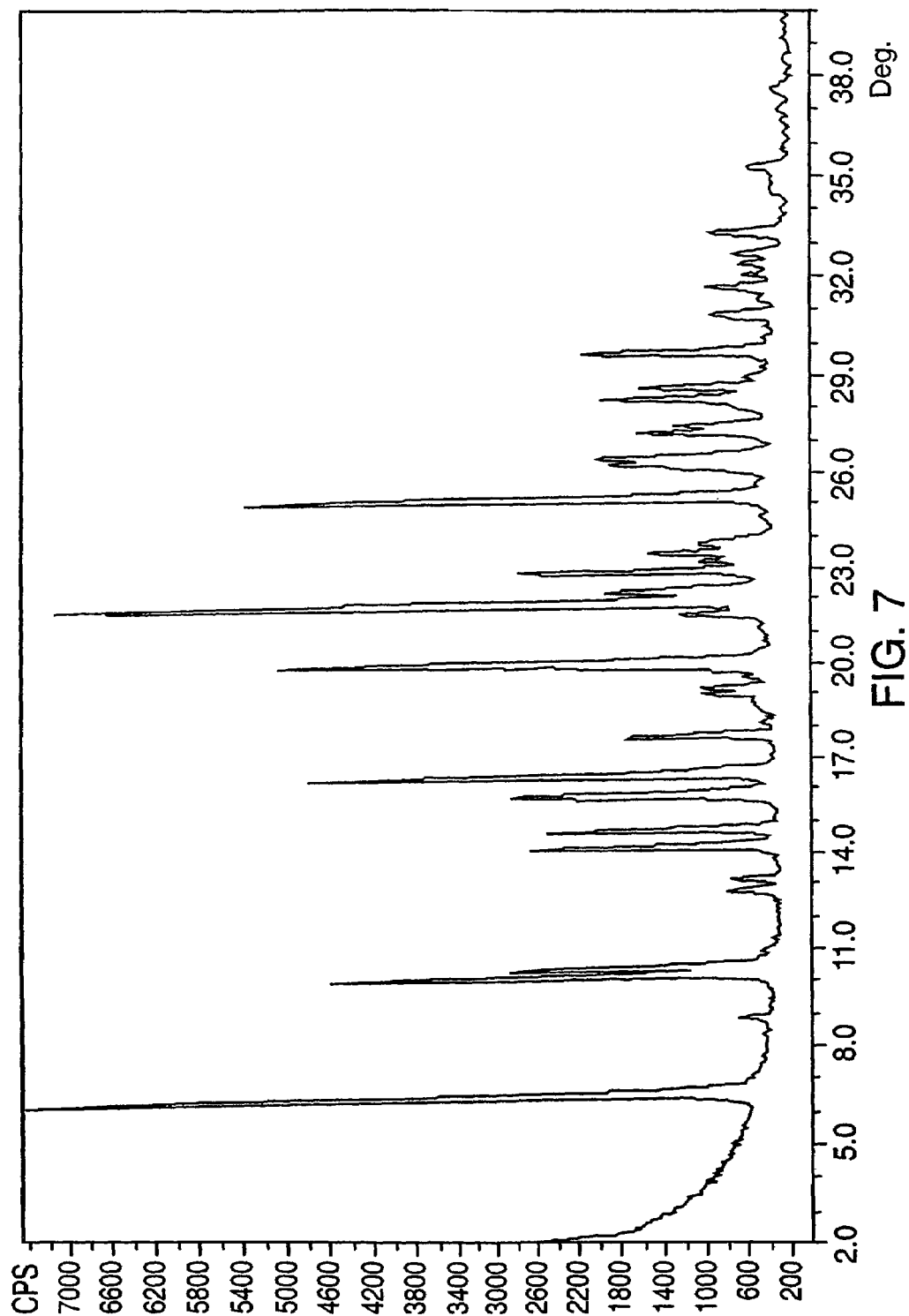
FIG. 7. shows the X-ray diffraction pattern of carvedilol HCl.

Crystalline Carvedilol HCl is characterized by an X-ray diffraction pattern with peaks at about 6.5±0.2, 10.2±0.2, 10.4±0.2, 14.2±0.2, 14.7±0.2, 15.8±0.2, 16.4±0.2, 17.7±0.2, 20.0±0.2, 21.5±0.2, 21.9±0.2, 22.2±0.2, 22.9±0.2, 25.2±0.2, 25.3±0.2, 27.2±0.2, 27.4±0.2, 28.2±0.2, 28.6±0.2, 29.6±0.2 degrees two theta. The most characteristic peaks of crystalline carvedilol HCl are at about 6.5±0.2, 10.2±0.2, 10.4 ±0.2, 15.8±0.2, 16.4±0.2 and 22.2±0.2 degrees two-theta. The diffraction pattern is reproduced in FIG. 7.

The DTG thermal profile of carvedilol HCl shows two endothermic peaks. A peak at 118° C. is a dehydration peak. A second peak endothermic peak at 135° C. is due to melting of the sample. LOD for this sample is 3.5%. The Water content of this sample as measured by Karl-Fisher analysis is 3.7%. Thus the Karl-Fisher analysis is in agreement with LOD value, and confirm the presence of hydrate in this sample. The expected value for carvedilol HCl monohydrate is 3.9%

A Pharmaceutical Composition Containing Carvedilol

According to another aspect, the present invention relates to a pharmaceutical composition comprising one or more of the novel crystal forms of carvedilol disclosed herein and at least one pharmaceutically acceptable excipient. Such pharmaceutical compositions may be administered to a mammalian patient in a dosage form.

The dosage forms may contain one or more of the novel forms of carvedilol or, alternatively, may contain one or more of the novel forms of carvedilol as part of a composition. Whether administered in pure form or in a composition, the carvedilol form(s) may be in the form of a powder, granules, aggregates or any other solid form. The compositions of the present invention include compositions for tableting. Tableting compositions may have few or many components depending upon the tableting method used, the release rate desired and other factors. For example, compositions of the present invention may contain diluents such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents such calcium carbonate and calcium diphosphate and other diluents known to one of ordinary skill in the art. Yet other suitable diluents include waxes, sugars (e.g. lactose) and sugar alcohols like mannitol and sorbitol, acrylate polymers and copolymers, as well as pectin, dextrin and gelatin.

Other excipients contemplated by the present invention include binders, such as acacia gum, pregelatinized starch, sodium alginate, glucose and other binders used in wet and dry granulation and direct compression tableting processes; disintegrants such as sodium starch glycolate, crospovidone, low-substituted hydroxypropyl cellulose and others; lubricants like magnesium and calcium stearate and sodium stearyl fumarate; flavorings; sweeteners; preservatives; pharmaceutically acceptable dyes and glidants such as silicon dioxide.

Dosage forms may be adapted for administration to the patient by oral, buccal, parenteral, ophthalmic, rectal and transdermal routes. Oral dosage forms include tablets, pills, capsules, troches, sachets, suspensions, powders, lozenges, elixirs and the like. The novel forms of carvedilol disclosed herein also may be administered as suppositories, ophthalmic ointments and suspensions, and parenteral suspensions, which are administered by other routes. The most preferred route of administration of the carvedilol forms of the present invention is oral.

Capsule dosages will contain the solid composition within a capsule which may be coated with gelatin. Tablets and powders may also be coated with an enteric coating. The enteric-coated powder forms may have coatings comprising phthalic acid cellulose acetate, hydroxypropylmethyl cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

The currently marketed form of carvedilol is available as a 3.125 mg, a 6.25 mg, a 12.5 mg, and a 25 mg tablet which includes the following inactive ingredients: colloidal silicon dioxide, crospovidone, hydroxypropyl methylcellulose, lactose, magnesium stearate, polyethylene glycol, polysorbate 80, povidone, sucrose, and titanium dioxide.

The function and advantage of these and other embodiments of the present invention will be more fully understood from the examples below. The following examples are intended to illustrate the benefits of the present invention, but do not exemplify the full scope of the invention.

EXAMPLES

Example 1

Preparation of Carvedilol in Neat Conditions 2-(2-Methoxyphenoxy)ethylamine (III) (4.89 g) was heated to about 100° C., after which 4-(oxiran-2-ylmethoxy)-9H-carbazole (II) (3.31 g) was added portionwise. After approximately 20 minutes, the reaction mixture was cooled to about 70° C., after which water (25 ml) and ethyl acetate (15 ml) were added. The pH of the two-phase mixture was then adjusted to 5 with 2 N hydrochloric acid. The solid that formed, Carvedilol hydrochloride hydrate, is filtered, washed with water (20 ml) followed with ethylacetate (15 ml). The resulting material is reslurried in ethylacetate (50 ml) and water (20 ml) containing 5% Sodium carbonate until the pH reached 7.5. The organic phase was separated and dried over sodium sulfate. The dried solution was concentrated to a turbid solution and cooled overnight to about 4° C. Precipitated carvedilol was isolated by filteration and crystallized from isopropanol.

Example 2

Preparation of Carvedilol in Neat Conditions 2-(2-Methoxyphenoxy)ethylamine (m) (4.89 g) was heated to about 100° C., after which 4-(oxiran-2-ylmethoxy)-9H-carbazole (II) (3.31 g) was added portionwise. After approximately 20 minutes, the reaction mixture was cooled to about 70° C., after which water (25 ml) and ethyl acetate (15 ml) were added. The pH of the two-phase mixture was then adjusted to 5 with 2 N hydrochloric acid. The solid that formed, Carvedilol hydrochloride hydrate, is filtered, washed with water (20 ml) followed with ethylacetate (15 ml).

The resulting material is reslurried in ethylacetate (50 ml) and water (20 ml) containing 5% Sodium carbonate until the pH reached 7.5. The organic phase was separated and dried over sodium sulfate. The dried solution was concentrated to a turbid solution and cooled overnight to about 4° C. Precipitated carvedilol was isolated by filteration and crystallized from methanol.

Example 3

Process for Preparing Form I of Carvedilol

Crystalline carvedilol is prepared according to the procedure in Example 3. The crystalline material is then dried at 50-60° C. for 6 hours. The dried crystalline carvedilol (220 g carvedilol) is dissolved in 2200 ml Ehtyl Acetate. The ethyl acetate solution is heated with agitation to 77° C. until the solid is completly dissolved. The ethyl acetate solution was then cooled with agitation to about 50° C. in a time period of 15 min. Te cooled solution was stirred for 48 hours. The solution was then cooled to 10° C. in 0.75 hours with agitation. After stirring the suspension for additional 24 hours, the product was filtered. Pure Crystalline carvedilol Form I (170 g) was obtained.

Example 4

Preparation of Crystalline Carvedilol Form II

Crystalline carvedilol Form II is formed by crystallizing carvedilol from the solvents listed in Table I. Carvedilol is crystallized by forming a solution of carvidilol heated to reach a clear solution, usually close to the solvent boiling temperature. The solution is then cooled to ambient temperature and the precipitate is filtered to yield Carvedilol for II.

TABLE I

| Solvent | Ratio of Solvent (ml): Carvedilol (g) |
|---|---|
| Methanol | 11 |
| Ethanol abs. | 12 |
| 1-propanol | 14 |
| Isopropanol | 13 |
| n-Butanol | 11 |
| Ethylen glycol | 13 |
| Ethyl-acetate | 10 |
| Butyl Acetate | 12 |
| isobutyl methl ketone | 12 |
| Dichloromethane | 12 |
| Dichloroethane | 25 |
| Acetonitile | 50 |
| Acetone | 25 |

Example 5

Preparation of Crystalline Carvedilol Form II by Filtration at −20° C.

Crystalline carvedilol Form II is formed by crystallizing carvedilol from the solvents listed in Table II. Carvedilol is crystallized by forming a solution of carvidilol heated to about the solvent boiling temperature. The solution is then cooled to −20° C., the precipitate is filtered and dried to yield Carvedilol Form II.

TABLE II

| Solvent | Ratio of Solvent (ml): Carvedilol (g) [Please Confirm Units] |
|---|---|
| Isoamylalcohol | 50 |
| Toluene | 53 |
| Xylene | 51 |

Example 6

Preparation of Crystalline Carvedilol Form II in Solvent Mixtures

Crystalline carvedilol Form II is formed by crystallizing carvedilol from the mixture of solvents listed in Table III. Carvedilol is crystallized by forming a solution of carvidilol heated to form a clear solution, usually close to the boiling temperature of the mixture of solvent. The solution is then cooled to ambient temperature and filtered. The crystals are collected by filtration and dried to yield Carvedilol form II.

TABLE III

| Solvent | Solvents ratio | Ratio Solvent (ml): Carvedilol (g) [Please Confirm Units] |
|---|---|---|
| Acetone: Cyclohexane | 1:4.8 | 230 |
| Chloroform: Cyclohexane | 1:3 | 130 |
| Dichloroethane: cyclohexane | 1:2.5 | 142 |
| Dichloromethane: Cyclohexane | 1:1.7 | 90 |
| Pyridine: Cyclohexane | 1:3.5 | 45 |
| Tetrahydrofurane: Cyclohexane | 1:2.5 | 53 |
| Dioxane: Cyclohexane | 1:2.3 | 70 |
| Acetone:Hexane | 1:2 | 235 |
| Chloroform: hexane | 1:1.5 | 87 |
| Dichloroethane: Hexane | 1:1.2 | 89 |
| Dichloromethane: hexane | 1:1.6 | 90 |
| Tetrahydrofuran: Hexane | 1:3 | 49 |
| Ethanol:Hexane | 1:3.8 | 145 |

Example 7

Preparation of Crystalline Carvedilol Form III

Carvedilol (4 g) was dissolved in 45 mL of a mixture of 96% Ethanol and 4% water by heating the mixture under stirring in a 55° C. water bath. The solution was cooled and left at room temperature without stirring for about 14 hours, the crystals were filtered through a buchner funnel, rinsed twice with about 10 ml cold (4° C.) 96% ethanol, and dried in a desiccator at room temperature (connected to air pump) until constant weight to yield carvedilol Form III.

Example 8

Preparation of Crystalline Carvedilol Form III

Carvedilol (4 g) was dissolved in 195 mL mixture of water/methanol (in a ratio 1:3 respectively ) by heating the mixture under stirring in 55° C. water bath. The solution cooled to ambient temperature and left at ambient temperature without stirring for about 15 h, the crystals were filtered through a buchner and dried in a desiccator at room temperature (connected to air pump) until constant weight to yield carvedilol Form III.

Example 9

Preparation of Crystalline Carvedilol Form III

Carvedilol (4 g) was dissolved in 39 mL pyridine by stirring at room temperature. 70 mL of water was then added dropwise until crystallization began. The solution was left at room temperature without stirring for about 80 h, then the crystals were filtered through a buchner and dried in a desiccator at room temperature (connected to air pump) until constant weight to yield Carvedilol Form III.

Example 10

Preparation of Crystalline Carvedilol Form III

Carvedilol (4 g) was dissolved in 76 mL dioxane at room temperature, and 110 mL of water were added in portions of about 10 mL to the stirred solution. The resulting solution was left at room temperature without stirring for about 15 h, then the crystalline precipitate which had formed was filtered through a buchner funnel and dried in desiccator at room temperature (connected to air pump) until constant weight to yield Carvedilol Form III in a mixture with Carvedilol Form II.

Example 11

Preparation of Crystalline Carvedilol Form III

Carvedilol (4 g) was dissolved in 267 mL dioxane/water in the ratio 1:1.4 respectively by heating the mixture under stirring at 55° C. water bath. The resulting solution was left at room temperature without stirring for about 15 h then the crystals were filtered through a buchner funnel and dried in a desiccator (connected to air pump) until constant weight to yield Carvedilol Form III in a mixture with Carvedilol Form II.

Example 12

Preparation of Crystalline Carvedilol Form III

Carvedilol (4 g) was dissolved in 180 ml, Hexane/IPA in a ratio 1:1 by heating the mixture under stirring at 55° C. water bath. The solution was allowed to sit at room temperature without stirring for about 15 h, then the resulting crystals were filtered through a buchner funnel and dried in a desiccator (connected to air pump) at room temperature until constant weight to yield Carvedilol Form III.

Example 13

Process for Preparing Form III of Carvedilol

Carvedilol (40 g) was dissolved in 150 ml of ethanol and 40 ml water. The solution was heated with agitation to 60-70° C. until the solid material was completely dissolved. The solution is then cooled with agitation to 10° C. over a period of 3 hours. After stirring the suspension for an additional 2.75 hours, the product is filtered. Pure Carvedilol Form III (35 g) was obtained.

Example 14

Preparation of Crystalline Carvedilol Form IV

Carvedilol (1 g) was dissolved in 35 mL methyl ethyl ketone by stirring at room temperature, and 202 mL cyclohexane was added dropwise. The solution was left at room temperature without stirring for about 15 h, then the resulting crystals were filtered through a buchner funnel and dried in a desiccator at room temperature (connected to air pump) until constant weight to yield carvedilol Form IV.

Example 15

Preparation of Crystalline Carvedilol Form V

Carvedilol (1 g) was dissolved in 70 mL methyl ethyl ketone by stirring at room temperature, and 138 mL hexane were added dropwise. The solution was left at room temperature without stirring for about 15 h, then the resulting crystals were filtered through a buchner funnel and dried in a desiccator at room temperature (connected to air pump) until constant weight to yield carvedilol Form V.

Example 16

Preparation of Crystalline Carvedilol Form V

Carvedilol (2 g) was dissolved in 45 mL methyl ethyl ketone by heating the mixture under stirring at 55° C. water bath, then the solution was cooled and left at room temperature without stirring for about 14 hours, the crystals were filtered through a buchner funnel and dried in a desiccator at room temperature (connected to air pump) until constant weight to yield carvedilol Form V.

What is claimed is:

1. A method for preparing crystalline carvedilol Form II, comprising the steps of:
   a) forming a solution of carvedilol by dissolving carvedilol in a solvent mixture;
   b) precipitating carvedilol Form II by cooling the solution to about −20° C.; and,
   c) isolating crystalline carvedilol Form II.

2. The process of claim 1, wherein the temperature of the solution is from about 40° C. to about the boiling temperature of the solvent.

3. The process of claim 1, wherein the precipitated carvedilol Form II is isolated by filtration.

4. The process of claim 1, wherein the solution is cooled to a temperature from about −20° C. to ambient temperature.

5. The method of claim 1, wherein the solvent mixture is selected from the group consisting of acetone:cyclohexane, chloroform:cyclohexane, dichloroethane:cyclohexane, dichloromethane:cyclohexane, pyridine:cyclohexane, tetrahydrofurane:cyclohexane, dioxane:cyclohexane, acetone:hexane, chloroform:hexane, dichloroethane:hexane, dichloromethane:hexane, tetrahydrofuran:hexane and ethanol:hexane.

* * * * *

UNITED STATES PATENT AND TRADEMARK OFFICE
CERTIFICATE OF CORRECTION

PATENT NO. : 7,485,663 B2  Page 1 of 1
APPLICATION NO. : 11/217643
DATED : February 3, 2009
INVENTOR(S) : Hildesheim et al.

It is certified that error appears in the above-identified patent and that said Letters Patent is hereby corrected as shown below:

Column 16, line 46-47, change "tetrahydrofurane" to -- tetrahydrofuran --

Signed and Sealed this

Sixteenth Day of March, 2010

David J. Kappos
*Director of the United States Patent and Trademark Office*